United States Patent [19]

Korpman

[11] 4,318,408
[45] Mar. 9, 1982

[54] ABSORBENT PRODUCTS
[75] Inventor: Ralf Korpman, Bridgewater, N.J.
[73] Assignee: Permacel, New Brunswick, N.J.
[21] Appl. No.: 88,881
[22] Filed: Oct. 29, 1979
[51] Int. Cl.³ .................................... A61F 13/16
[52] U.S. Cl. ............................ 128/287; 128/285; 128/290 P; 128/290 B
[58] Field of Search ............ 128/284, 287, 155, 156, 128/285, 290 R, 290 P, 290 B, 296

[56] References Cited
U.S. PATENT DOCUMENTS

| | | | |
|---|---|---|---|
| 3,070,095 | 12/1962 | Torr | 128/284 |
| 3,347,236 | 10/1967 | Torr | 128/284 |
| 3,586,645 | 6/1971 | Granger et al. | 128/284 |
| 3,669,103 | 6/1972 | Harper | 128/156 |
| 3,670,731 | 6/1972 | Harmon | 128/284 |
| 3,686,024 | 8/1972 | Nankee et al. | 128/284 |
| 3,888,257 | 6/1975 | Cook et al. | 128/296 |
| 3,890,974 | 6/1975 | Kozak | 128/287 |
| 3,900,027 | 8/1975 | Keedwell | 128/284 |
| 3,900,378 | 8/1975 | Yen et al. | 128/284 |
| 3,935,099 | 1/1976 | Weaver et al. | 260/17.4 GC |
| 3,957,362 | 5/1976 | Mancini et al. | 128/130 |
| 3,959,569 | 5/1976 | Burkholder | 428/475 |
| 3,966,679 | 6/1976 | Gross | 260/47 EA |
| 3,997,484 | 12/1976 | Weaver et al. | 260/17.4 GC |
| 4,026,849 | 5/1977 | Bagley et al. | 260/17.4 GC |
| 4,102,340 | 7/1978 | Mesek et al. | 128/287 |
| 4,105,033 | 8/1978 | Chatterjee et al. | 128/285 |
| 4,156,664 | 5/1979 | Skinner | 260/17.4 GC |
| 4,235,237 | 11/1980 | Mesek et al. | 128/284 |

OTHER PUBLICATIONS

"Superabsorbents Seek Markets that are Super", Chemical Week, Jul. 18, 1979, p. 40.

Primary Examiner—Robert W. Michell
Assistant Examiner—T. J. Wallen
Attorney, Agent, or Firm—Alice O. Robertson

[57] ABSTRACT

A flexible non-disintegrative absorbent product comprising a water-insoluble substantially non-swelling matrix of an elastomeric polymer bearing a uniformly dispersed particulate water-insoluble water-swellable organic polymer absorbent. Certain compositions and processes for their preparation as well as articles prepared from the products are described.

8 Claims, 8 Drawing Figures

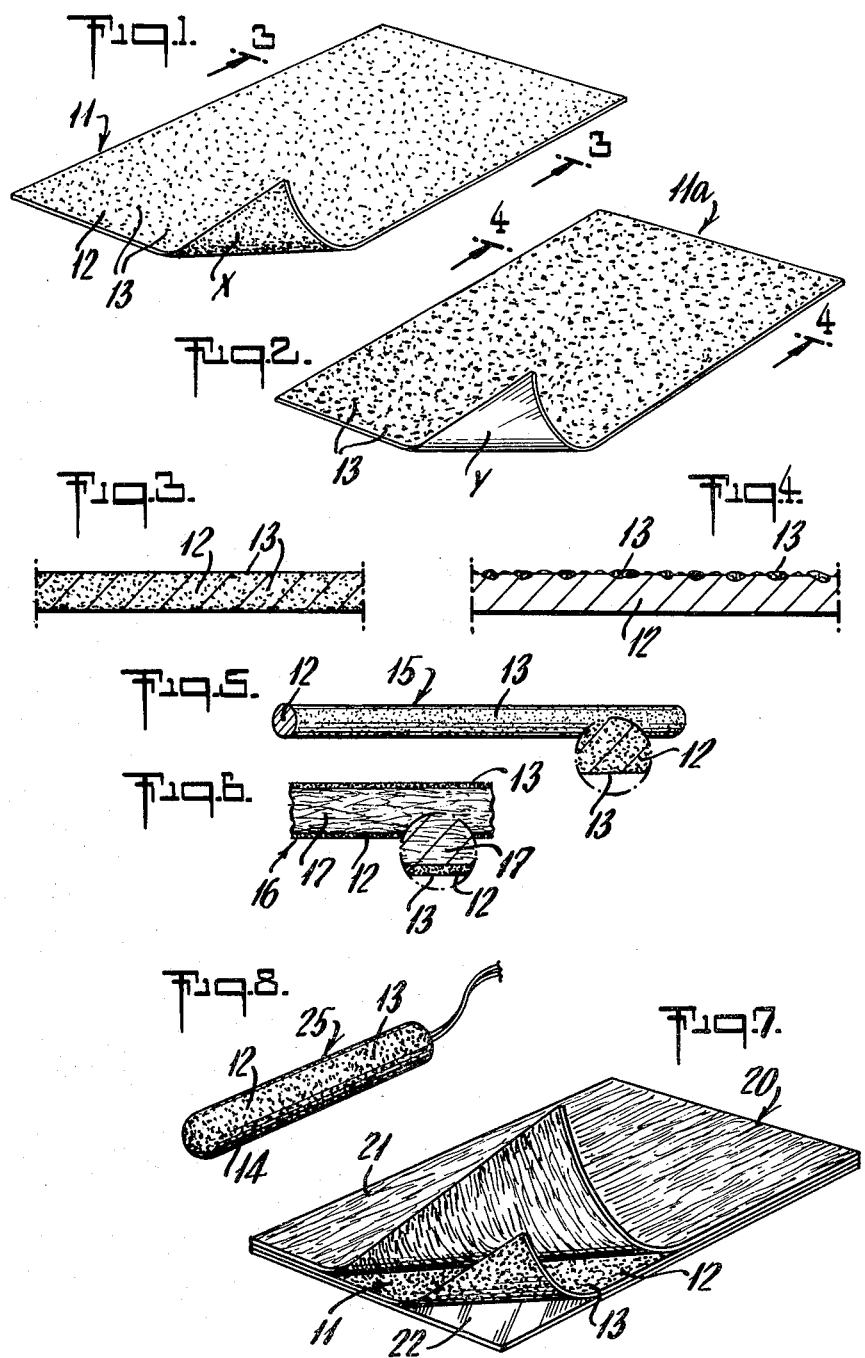

ABSORBENT PRODUCTS

The present invention relates in general to non-disintegrative aqueous-fluid-absorbent products, processes and compositions.

BACKGROUND OF THE INVENTION

Retention and or removal of water or aqueous liquids, particularly body fluids, are frequently accomplished by use of absorbent bearing materials and articles manufactured therefrom. Representative articles include diapers, incontinence pads, sanitary napkins, bibs, wound dressings and the like. Generally, absorption is achieved by use of cellulosic and modified cellulose materials. Where the intended use contemplates absorption of relatively large volumes of liquids such as diapers, sanitary napkins and the like, the cellulosic materials are in the form of fluff or batting. For these uses especially, there are teachings in the literature for distributing particulate materials, sometimes referred to in the art as superabsorbents, throughout the batting or in certain areas thereof. The settling and bunching of the powder or particulate matter encountered during shipping and storage have rendered these modifications of little value in actual practice. Also found in the art are teachings for modifying the fibers in the batting to greatly increase their absorbency. These modifications have not avoided the need for a batting. Free films of absorbent polymers have been described but they are generally stiff, non-flexible and frequently frangible. Some films have been reported which are flexible but methods for the production of these films employ aqueous medium either during or prior to extrusion with subsequent removal of water and do not constitute convenient or practical manufacturing operations where time-consuming drying operations necessary for removal of water are sought to be avoided. Absorbents have been distributed in latex but these films are also subject to similar manufacturing drawbacks. Very thin films of absorbent have been coated onto cellulosic fibrous backings which while operable when contained such as in a diaper with topsheet and backsheet are subject to disintegration when not contained. Additionally, absorbents have been incorporated in a foam matrix which may be useful for some applications but are not applicable for thin films or filaments. Although some suggestion has been made of water-insoluble polymeric sheet material broadly as support for absorbent, no actual product is reported or known to be available.

SUMMARY OF THE INVENTION

According to the present invention, there has been devised an aqueous-fluid-absorbent non-disintegrative product which comprises a water-insoluble substantially non-swelling matrix of a elastomeric polymer having at least partially imbedded therein, particulate water-insoluble but water-swellable organic polymer absorbent. By "water" as herein employed is meant aqueous fluids or liquids and is intended to include such fluids as saline, serum, blood, mucous as well as other aqueous solutions or dispersions. The matrix, preferably of thermoplastic-elastomeric polymer as subsequently defined, is insoluble and substantially non-swellable in aqueous systems and resistant to disintegration when wet. The absorbent is selected from organic polymers which are insoluble in water but which are swellable and which absorb many times their own weight of water or aqueous fluid. The organic polymer absorbents may be completely synthetic or may be selected from modified natural molecules, especially modified polysaccharide as hereinafter more fully described.

The product is flexible and elastic, is resistant to disintegration when wet, is manufactured in the absence of water, can be made very thin while still being highly absorbent, can be self-supporting or be a coating, can be made in many forms and/or shapes. The forms include film, monofilament, sheet, rope, tubing, etc. and as coating on a substrate, i.e., a supported film.

The product may be prepared by the several procedures which are used in the manufacture of films, filaments and the like. The matrix polymer and the polymer absorbent comprise novel compositions suitable in certain of the methods of preparation and these compositions as well as the use of these compositions in preparing the products constitute an aspect of the present invention.

The absorbent product has numerous applications and is adaptable for use in protective coverings, sanitary napkins, wound dressings, diapers, bed pads, incontinence pads, packaging materials, agricultural blankets and the like. Certain articles which may be prepared employing the novel absorbent bearing polymer products also constitute an aspect of the present invention.

BRIEF DESCRIPTION OF THE DRAWINGS

FIG. 1 is a perspective view of an absorbent product in the form of a film and having absorbent dispersed throughout.

FIG. 2 is a partial perspective view of an absorbent product in the form of a film with absorbent on one surface of the film.

FIG. 3 is a partial sectional elevation taken along 3—3 in FIG. 1.

FIG. 4 is a partial sectional elevation taken along 4—4 in FIG. 2.

FIG. 5 is an enlarged partial sectional view showing an embodiment of the invention when the absorbent product is in the form of a monofilament.

FIG. 6 is a partial sectional view showing an elongated core coated with the absorbent product.

FIG. 7 is a perspective view of a diaper employing the absorbent product.

FIG. 8 is a view of a tampon made of the absorbent product.

DESCRIPTION OF THE PREFERRED EMBODIMENTS

The absorbent product of the present invention has particulate water-insoluble but water-swellable organic polymer absorbent dispersed on the surface or throughout a water-insoluble substantially non-swelling matrix. In the preferred embodiments, the particles are dispersed in a manner such that the absorbent is partially imbedded in the matrix. By "partially imbedded" is meant that most of the particles of the organic polymer absorbent have a portion of the particle surface exposed or protruding above at least one surface of the matrix. Although some individual particles may be completely imbedded, they are generally in a contiguous relationship to particles which are exposed to a surface. In one embodiment of the present invention the particles are dispersed throughout the matrix so that the particles are distributed within the matrix and are exposed to all surfaces of the matrix; in another embodiment, the particles are distributed on one surface of the matrix.

The foregoing may be better understood by reference to the drawings. FIGS. 1 and 3 show a product in the form of a film 11 in which the absorbent particles 13 is dispersed throughout the matrix 12. It can be seen from the area "X" in FIG. 1, representing the underside of the film, that there is absorbent exposed on the underside as well as on the top surface. FIGS. 2 and 4 show a product in the form of a film 11a in which the absorbent 13 is on one surface of matrix 12. The area "Y" in FIG. 2 shows no absorbent exposed on the underside surface. FIG. 5 illustrates absorbent dispersed throughout the matrix when the product is a monofilament or a single strand rope. FIG. 6 illustrates the product in the form of a coating 16 on a core substrate 17.

The particulate absorbent materials are non-fibrous substances in the form of fine, discrete particles which cannot be formed into a fabric web. The particles can have various shapes such as spherical, rounded, angular, acicular, irregular, fragmented and the like. They range in size from about 1 micron to as much as $2 \times 10^4$ microns in diameter or cross-section (largest dimension when not spherical), and are selected from those materials which are generally considered powders and those which are non-pulverous particulate matter. The expression, "powder" is employed to designate particles which are particle size of from about 1 to about $10^3$ microns. When the particulate materials are dispersed throughout and imbedded in the matrix they are preferably in the form of a powder. When employed in the form of powder and dispersed throughout, the presence of the particles is not always readily apparent; the film or filament oftentimes appears as a smooth film of the matrix polymer. In the embodiment in which the absorbent is borne on one surface of the film, the particles are preferably non-pulverous. The approximate shape and geometry of the particles are retained when the material swells to provide for the binding of the fluid therein.

The matrix is of a elastomeric polymer and preferably assumes a shape achievable by extrusion or solvent casting. Thus, it may be in the form of a film, sheet, filament, wire, rope, tube and the like. Since one of the advantages of the present invention is the rendering available of a very thin, highly flexible and elastic material of high absorption capacity, the preferred embodiments of the present invention contemplate use of thin film or fine monofilament as matrix. The matrix may have a thickness ranging from about 1 mil to about 60 mils. The thickness of the film is contemplated generally to be less than about 10 mils. Usually, it will be more than 1 mil, preferably in the range of about 2.5 to 5 mils. When the product is in the form of a filament or rope, the cross-sectional dimension may be from about 5 to about 60 mils. The expression "filament" as herein employed is also meant a monofilament without regard to the cross-sectional dimensions. Rope is intended to connote a single strand which is not twisted or braided. When the product is in the form of a coating on a substrate, the dimensions may be similar to those of unsupported film but generally will be thinner.

The product has a capacity to absorb water or aqueous fluid in an amount of at least 3 times, preferably from about 15 to 40 times or more of the weight of the absorbent in the product. Since the absorptive capacity of the product is dependent on the amount of absorbent in the product, the absorptive capacity of the product depends on the density or on the weight of the absorbent incorporated into a given volume of the matrix. The particulate absorbent material is used in the product in the range of from about 5 to 200 parts, preferably from about 50 to 100 parts, for every 100 parts by weight of the matrix polymer. The product efficiently absorbs water and aqueous fluids while retaining elasticity and flexibility, and is resistant to loss of water when subject to pressure.

The particulate absorbent materials to be dispersed in the matrix are organic polymers which may be wholly synthetic organic polymers or which may be modified polysaccharides. In these absorbent polymers, hydrophilic groups constitute at least 25 percent and up to about 72 percent of their molecular structure and the polymeric network has been lightly cross-linked to introduce a limited water-insolubility into the molecule. Suitable water-insoluble materials have a minimum average molecular weight per cross-linkage of about 13,000 and a maximum molecular weight per cross-linkage of about 276,000. These materials are frequently spoken of in the art as "hydrogels" or "hydrocolloid polymers," and further as "superabsorbents." The preferred polymers have an acrylate group in their molecular structure. They may be completely synthetic acrylate polymers or acrylate modified polysaccharides, e.g., acrylate modified starch or acrylate modified cellulose. "Acrylate polymers" or "polyacrylate" as herein employed embrace not only acrylate salts but also those in which a portion of the hydrophilic group is acrylamide, acrylic acid or acrylate ester. Alternatively, the hydrophilicity may be supplied by a different type of hydrophilic group such as sulfonate, oxide, etc., or by a different type of polymer as hereinafter detailed. Carboxymethylcellulose after cross-linking is also within a scope of suitable absorbents. The absorbent is typically a cross-linked natural or synthetic polymer which without the cross-linking would be water-soluble but which has been lightly cross-linked in ways known in polymer syntheses. The preferred absorbents are cross-linked polymers belonging to one of the following: completely synthetic acrylate polymer, acrylate modified starch, acrylate modified cellulose, and cross-linked carboxymethylcellulose.

Considering first the preparation of the completely synthetic absorbents, it is immaterial in the present invention whether the polymers here to be employed be prepared by supplying appropriate monomer or monomers and thereafter polymerizing, or by polymerizing and thereafter modifying a part of the resulting polymer with recurring moieties. Thus, the polymers may be prepared by cross-linking a preformed water-soluble straight chain polymer, by polymerizing an appropriate monomer or monomer and co-monomer and effecting both polymerization and cross-linking, or by incorporating an appropriate group in the polymer structure after completion of the polymerization. An example of the latter is sulfonation after polymerization to obtain polymers bearing sulfonic moieties. Moreover, where it is desired to have the salt form of the carboxylic or sulfonic group, the polymer may be first prepared as an acid, ester, amide or nitrile and the product hydrolyzed in whole or in part.

The preferred of the synthetic absorbents are the acrylate type absorbent which includes not only the acrylate salts and acids but also those which have been represented in the literature, e.g., U.S. Pat. No. 3,686,024, by the following formula:

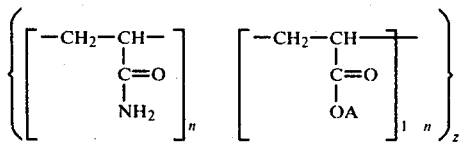

where A is an alkali metal ion such as sodium or potassium, or hydrogen, n is 0.5 to about 0.9, 1−n defines the extent of hydrolysis, and z is the number of mer units between cross-links.

The latter type of acrylate absorbent may be prepared by polymerizing an about 2 to 20 weight percent aqueous solution of acrylamide with from about 0.005 to 0.5 mole percent (based on acrylamide) of a difunctional organic cross-linker such as N,N'-methylenebisacrylamide soluble in the aqueous monomer system in the presence of free radical catalysts to obtain a water-swellable cross-linked polyacrylamide, and thereafter partially hydrolyzing in aqueous alkali to obtain a cross-linked polymer having both carboxamide and alkali metal carboxylate groups as more fully described in U.S. Pat. No. 3,247,171. Alternatively, a linear polyacrylamide may be cross-linked with a cross-linking compound such as N,N'-methylenebisacrylamide, 1,4-divinylbenzene, diallylamine, N,N-diallylmethacrylamide and the like, and thereafter hydrolyzing. A polymer having both carboxamide and carboxylate group also may be made by copolymerizing acrylamide and acrylic acid alkali metal sal in the presence of cross-linking monomer such as N,N-methylenebisacrylamide in the presence of catalyst system such as equal parts of ammonium persulfate and β-dimethylaminopropionitrile, also described in the aforesaid patent. The former type may be prepared by subjecting a mixture of a monovalent cation salt of acrylic acid in water to the influence of high energy ionizing radiation cross-linking as more particularly described in U.S. Pat. No. 3,229,769, or subject it to chemical cross-linking as described in British Pat. No. 719,330. A number of suitable acrylate absorbents are available commercially, such as PERMASORB (National Starch and Chemical), SAN-WET (Sanyo), "5388" designation (Goodrich), AQUA-KEEP (Mitsubishi), and is also obtainable from The Dow Chemical Company.

Another type of completely synthetic absorbent is a cross-linked poly(alkylene oxide) of molecular weight of at least 100,000 which may be prepared by contacting poly(alkylene oxide) with a suitable cross-linking agent in the presence of a free radical catalyst in a liquid medium containing solvent-non-solvent mixture for poly(alkylene oxide) wherein the nonsolvent portion constitutes at least 35 percent by weight of the liquid medium at a temperature sufficiently high to effect cross-linking as more fully described in U.S. Pat. No. 3,956,224. Alternatively, poly(alkylene oxide) may be cross-linked by ionizing radiation as described in U.S. Pat. No. 3,264,202, or co-cross-linked with at least one other water-soluble polymer by exposing aqueous systems of the polymers to high energy radiation to produce cross-linked water-soluble absorbent polymers as more fully described in U.S. Pat. Nos. 3,957,605 and 3,898,143.

Still another type of completely synthetic polymer absorbent is cross-linked polystyrene sulfonates prepared by known procedures, e.g., by copolymerizing styrene with a non-conjugated divinyl compound such as divinylbenzene in the presence of a polymerization catalyst such as benzoyl peroxide, preferably in the presence of a suspension stabilizer such as gelatin or polyvinyl alcohol, to produce a polymer which is then sulfonated by heating in the presence of concentrated sulfuric acid at a temperature of about 100° C.

Other suitable completely synthetic polymer absorbents include the poly(N-vinylpyrrolidone) type described in U.S. Pat. No. 3,669,103, polyurethane hydrogels described in U.S. Pat. Nos. 3,939,105 and 3,939,123. Still other suitable absorbents are represented by those named in U.S. Pat. Nos. 3,669,103, 3,966,679 and 4,102,340.

Another type of particulate absorbent material suitable for the present purposes is of polysaccharides modified by having grafted thereon hydrophilic chains. By "hydrophilic chains" is meant a polymer chain obtained from monomers which have a water-soluble group or which become water-soluble on hydrolysis, e.g., carboxyl, sulfonic, hydroxyl, amide, amino, quaternary ammonium and hydrolysis products. Representatives of such modified polysaccharides are described in U.S. Pat. No. 4,076,663. Preferred polysaccharide have hydrophilic chains containing a carboxylate group alone or together with a carboxylic or carbamide group attached to starch or cellulose backbone. The modified polysaccharides are sometimes referred to in the literature as starch or cellulose graft copolymers; the preferred modified graft copolymers are polysaccharide acrylates, or starch or cellulose acrylates. In these polysaccharide acrylates, the hydrophilic chain is attached to the backbone of the cellulose or starch molecule through a carbon linkage. Thus, a modified cellulose may be represented by the formula

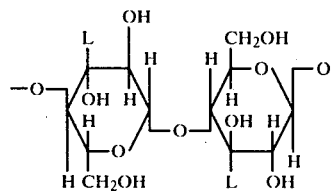

wherein L represents a hydrophilic chain of the general formula

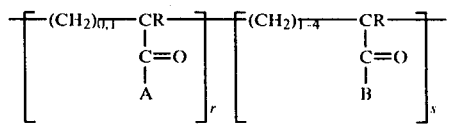

wherein

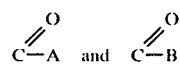

represents

acid, ester, alkali metal or ammonium salt, or amide groups, each R independently is hydrogen or lower alkyl, r is an integer of 0 to about 5000 and s is an integer of from 0 to about 5000, and r plus s is at least 500. A starch graft copolymer would be similar but would have a starch backbone. These polysaccharide acrylates may be prepared, for example, by polymerizing an appropriate polysaccharide with acrylonitrile or methacrylonitrile, with methyl or ethyl acrylate, with acrylic or methacrylic acid, or with acrylamide or methacrylamide, and thereafter hydrolyzing the resulting polymer in whole or in part with aqueous alkali. Alternatively, the polymer containing the carboxylate group may be prepared by polymerizing the alkali metal salt of acrylic or methacrylic acid. The procedures for carrying out graft-copolymerization of olefinically unsaturated chains onto cellulose and starch are well known in the art. Thus, grafting of the hydrophilic material onto a starch or cellulose backbone can be accomplished simultaneously with the formation of the hydrophilic polymeric material in an aqueous medium, because the peroxide catalyst used to copolymerize the various monomers forms a redox catalyst system in combination with a reducing agent and thus also serves to effect chain transfer onto the starch or cellulose backbone. Suitable reducing agents for this purpose are ceric ion, ferrous ion, cobaltic ion, $(NH_4)_2S_2O_8$, cuprous ion, and the like. The desired ions can be supplied in the form of salts such as ceric ammonium nitrate, ferrous ammonium sulfate, and the like. Graft copolymerization of olefinically-unsaturated chains can also be effected by irradiation (ultraviolet-, gamma, or X-radiation) or by heating in an aqueous medium in the presence of an emulsifier.

Powdered starch or cellulose fibers or pulp can be slurried in water containing a graft copolymerization catalyst system and the monomer or monomers added to the slurry and polymerized in situ at ambient temperature or above depending on the catalyst employed. In this manner a portion of the formed hydrophilic polymer may also be physically entrapped into the polysaccharide backbone material during the polymerization process. The preparation of suitable starting materials for practicing the present invention is also illustrated in U.S. Pat. Nos. 2,922,768, 3,256,372, 3,661,815, 3,935,009, 4,028,290, 4,076,663 and 4,105,033. Suitable starch polyacrylates are available commercially such as SGP 5025 (General Mills or Henkel) and STASORB (A. E. Staley).

Suitable polysaccharides acrylates are those in which the hydrophilic chain loading on the backbone is within the range of about 10 percent by weight to about 90 Percent by weight, preferably about 40 to about 80 percent by weight of the graft co-polymer. The polymers produced are dried at atmosphere pressure to dry off the water to produce a relatively stiff and brittle material which may be comminuted into powder of particle size of at least 1 micron. Preferably, the particles are no less than about 50 microns and no greater than about 1000 microns. Most preferably they are in the range of about 70 to about 325 microns.

A fourth type of absorbent suitable in the present invention is cross-linked carboxymethyl cellulose (CMC). Suitable cross-linked carboxymethyl cellulose are those which may be prepared by heat treatment or wet cross-linking of the sodium salt of carboxymethylcellulose having from about 0.5 to about 1 carboxymethyl group for each anhydroglucose unit. In wet cross-linking, reagents bifunctional with respect to cellulose such as epichlorohydrin may be employed.

A representative method for the preparation of absorbent of the class cross-linked carboxymethylcellulose is heating finely divided particulate form of water-soluble alkali metal salt of carboxymethylcellulose having from about 0.5 to about 1 carboxymethyl group for each anhydroglucose unit to a temperature between about 130° C. and about 210° C., generally from a few minutes to several hours to obtain products which retain their physical appearance when dry but when suspended in water show reduced solubility and a new capacity of absorbing water to form swollen gel particles as more fully described in U.S. Pat. No. 2,639,239. The particles, if not of desired size, may be comminuted to powder of particle size preferably in the range of about 50 microns to 1000 microns. Suitable cross-linked carboxymethylcellulose are available as AQUASORB from Hercules.

The matrix in the absorbent product of the present invention comprises an elastomer, preferably a thermoplastic elastomeric block copolymer but also may be natural rubber, synthetic rubbers such as styrenebutadiene rubber, and the like which are elastic and which have glass transition temperature below about $-10°$ C.

The thermoplastic-elastomeric block copolymers are those having a thermoplastic block conventionally designated as A blocks and rubbery blocks conventionally designated as B blocks. One suitable group of block copolymers include those having thermoplastic endblocks and rubbery midblocks and designated as A-B-A block copolymers. The expression "A-B-A" block copolymer is intended to embrace all variations of block copolymers with rubbery midblocks and thermoplastic endblocks. Thus, it is intended to embrace copolymers sometimes designated A-B-C block copolymer in which C is also a thermoplastic endblock but of a different polymer than A. It is also intended to embrace linear, branched and radial block copolymers. The radial block copolymers may be designated $(A-B)_nX$ wherein X is a polyfunctional atom or molecule and in which each (A-B) radiates from X in a way that A is an endblock. Another suitable group of block copolymers include those in which B forms one endblock rather than a midblock and which are sometimes referred to as "A-B" or "simple" block copolymers. The expression "block copolymer" without qualification is intended to embrace both A-B-A and A-B type of copolymers.

The thermoplastic "A" block is generally a polymer of alkenylarenes, preferably of styrene or styrene homologs and analogs such as α-methylstyrene, 5-tertiary-butylstyrene, 4-methylstyrene, 3,5-diethylstyrene, 3,5-di-n-butylstyrene, 4-(4-phenyl-n-butyl)styrene, 2-ethyl-4-benzylstyrene, 4-cyclohexylstyrene, 4-n-propylstyrene vinyltoluene and the like.

The rubbery "B" block is a polymer of a conjugated lower aliphatic diene of from 4 to about 6 carbon atoms or of a lower alkene of from 2 to about 6 carbon atoms. Suitable conjugated dienes include butadiene, isoprene, 1,3-pentadiene, 1,3-hexadiene, 2,3-dimethylbutadiene and the like. The preferred dienes are butadiene and isoprene. Suitable alkenes include ethylene, butylene, propylene and the like.

In the radial block copolymer, $(A-B)_nX$, X may be an organic or inorganic polyfunctional atom or molecule and n is an integer having the same value as the functional group originally present in X. It is usually at least 3 and is frequently 4 or 5 but is not limited thereto. In addition, it embraces a more complex radial block copolymer system disclosed in the article, "New Rubber is Backed by Stars," appearing in Chemical Week, June 11, 1975, page 35.

Suitable thermoplastic rubber block copolymers are prepared by stepwise solution polymerization of the components. The preparations and properties of block copolymers are amply described in the literature such as, for example, "Thermoplastic Rubber (A-B-A Block Copolymers) in Adhesives" by J. T. Harlan et al., in "Handbook of Adhesives" edited by Irving Skeist, Van Nostrand Reinhold Co., New York, Second Edition (1977), pages 304–330; "Rubber-Related Polymers, I. Thermoplastic Elastomers" by W. R. Hendricks et al, in "Rubber Technology" edited by Maurice Morton, Van Nostrand Reinhold Co., New York (1973), pages 515–533; and U.S. Pat. Nos. 3,321,635; 3,519,585; 3,787,531; and 3,281,383; and for A-B block copolymers, U.S. Pat. Nos. 3,519,585 and 3,787,531.

In the suitable block copolymers, the individual "A" block portion has a number average molecular weight of at least 6,000, preferably in the range of from about 8,000 to 30,000 and the "B" block portion has a number average molecular weight preferably in the range of from about 45,000 to about 180,000. The "A" blocks constitute from about 5 to about 50 percent, preferably about 10 to about 30 percent by weight of the block copolymer. The number average molecular weight of the block copolymer is preferably in the range of about 75,000 to 200,000 for linear copolymers and preferably in the range of about 125,000 to 400,000 for radial copolymers.

When the "A" block is polystyrene and the "B" block is a polymer of butadiene, the polymer may be referred to as an S-B-S or S-B polymer, and when the "A" block is a styrene polymer and the "B" block is an isoprene polymer, the polymer may be referred to as an S-I-S or S-I polymer. Many of the block copolymers are obtainable commercially under trade names such as Kraton ® 1102 and 1107 (both linear Shell Chemical Co.), Solprene ® 418 and 420 (both radial), and Solprene ® 311X and 1205 (both simple; Phillips Petroleum Co.).

Embraced within the scope of thermoplastic elastomeric A-B-A or A-B block copolymers are certain of the alloys of A-B-A or A-B block copolymers as above defined and co-polyesters, such alloys being those having essentially elastic properties as disclosed and claimed in copending application, Ser. No. 54,540, filed July 5, 1979, in the name of Ralf Korpman and incorporated by reference. In the alloy, the co-polyester consists essentially of a polymeric ester of at least two different ester units, each ester unit being a condensation product of a dicarboxylic acid and an aliphatic diol. In these esters the dicarboxylic acids may be aromatic such as terephthalic acid and the like or aliphatic such as azelaic acid and the like and the aliphatic diols are preferably alkylene diols from 2 to 4 carbon atoms. The esters may be random, segmented or with alternating units, have torque properties of about 1000 to 5200 poises and have an average molecular weight in the range of 20,000 to 200,000. The alloys intended for the matrixes in the present invention are only those in which the A-B-A or A-B block copolymer is at least about 55 percent by weight and the co-polyester is correspondingly no greater than about 45 percent by weight.

The absorbent product of the present invention may be prepared by several methods none of which necessitate the use of an aqueous environment, thus eliminating the need for extended drying procedures. The preferred method may depend on the particular absorbent employed or whether it is desired to have the absorbent on one surface only.

When the absorbent is stable to the extrusion temperature of the matrix polymer and/or when the particulate absorbent is to be dispersed throughout the matrix, rather than on one surface, the product may be prepared by extrusion. Some of the absorbents which are extrudable polyacrylate as previously defined, sulfonated polystyrene, poly(alkylene oxide), and the like.

In employing the extrusion method, the matrix polymer and the absorbent polymer are thoroughly blended together and extruded. Preblending is highly desirable if there is to be a high loading of the absorbent. If the level of absorbent to be dispersed is low, i.e., about 5 to 15 parts by weight per 100 parts by weight of matrix polymer, the components may be fed directly into the extruder without preblending. However, it is preferred that the absorbent polymer and the matrix polymer be preblended with heating to a uniform dispersion of the particulate absorbent in the molten matrix polymer, and the resulting uniform blend after cooling be pelletized, crushed, flaked or otherwise reduced to a size suitable for feeding into an extruder or the molten blend be fed directly into the extruder and the extrusion carried out to obtain a non-disintegrative absorbent product comprising a water-insoluble substantially non-swelling matrix of a thermoplastic-elastomeric polymer having dispensed throughout, particulate, water-insoluble but water-swellable organic polymer absorbent in the form of a film, filament, tubing or other extrudable shape. In this method, the absorbent is preferably in the form of a powder, i.e., particle size of $10^3$ microns in diameter or less. The preblending preferably is carried out in the temperature range of from about 150° to 275° F. The extrusion is preferably carried out in the temperature range of from about 300° F. to about 450° F. The extrusion method is particularly suitable for obtaining non-disintegrative absorbent product in the form of very thin films and monofilaments. The product will have absorbent dispersed throughout as seen in FIGS. 1, 3 and 5 of the drawings.

The extrudable compositions which are preferably formed by pre-blending and comprising thermoplastic-elastomeric matrix polymer and particulate polymer absorbent constitute an aspect of the present invention. The composition may include minor amounts of materials generally added to extrudable film forming compositions. Representative of such additives are antioxidants such as 2,5-ditertiary-amylhydroquinone, zinc salts of alkyl dithiocarbamates; fillers and pigments such as zinc oxide, titanium dioxide, calcium carbonate, and the like. In addition to the conventional additives, small amounts of wetting agents may be included which will facilitate initiation of aqueous fluid uptake by the absorbent. Generally, the extrudable compositions comprise from about 5 to about 200 parts of polymer absorbent per 100 parts by weight of matrix polymer.

Preferred extrudable compositions are those which comprise synthetic polyacrylates and a thermoplastic-elastomeric A-B-A or A-B block copolymer matrix polymer. As previously indicated, the expression "acrylate" includes polymers which have any of acid ester, amide or salt acrylate groups or mixtures thereof. The compositions comprise from about 5 to about 200 parts of acrylate polymer per 100 parts of A-B-A or A-B block copolymer, preferably from about 20 to 100 parts.

The extrudable composition also may be employed in a hot melt casting technique. Thus, instead of cooling the molten blend and pelletizing for extrusion, the molten composition may be cast to produce a free film, or a coating on a substrate.

Another method by which a product may be uniformly dispersed throughout the matrix is particularly suitable for the preparation of film. This method contemplates a solvent casting composition in which the rubber or thermoplastic-elastomer, polymer absorbent and antioxidants are dispersed in an organic solvent. The composition is cast onto a suitable surface employing conventional methods, the solvent evaporated to obtain an elastic film having absorbent polymer uniformly dispersed throughout. Suitable solvents for the casting compositions are generally aromatic or paraffin hydrocarbons especially, toluene, xylene, benzene, heptane and the like. The compositions usually also contain antioxidants. Conventional antioxidants include zinc dibutyl dithiocarbamate, 2,5-ditertiary-butylhydroquinone, 2,5-ditertiary-amylhydroquinone and the like.

Absorbent products in which the particulate absorbent is to be supported by the matrix primarily on a surface may be prepared by a process in which the matrix is first formed and the absorbent incorporated thereon. This process is applicable in the preparation of the absorbent product regardless of the chemical nature of absorbent polymer employed.

One modification of this general procedure contemplates incorporation of the absorbent polymer substantially at the time of formation of the matrix. In this method, the matrix polymer is extruded into whatever shape is contemplated, generally, a film or a monofilament, and the absorbent is applied on the surface of the molten curtain or filament. The absorbent on contact becomes partially imbedded in the still molten surface and becomes permanently imbedded on cooling. The operation may be carried out by modification of the extrusion equipment in ways known in the art. For imbedding in a film, the particulate absorbent polymer may be spread or dusted on the film as it leaves the die. For incorporating on the surface of a filament, a similar procedure may be employed using a die adapter.

Another method employs a pre-formed matrix and the use of a solvent coating composition which has a solvent effect on the surface of the matrix allowing partial imbedding of the absorbent simultaneously with adhesion, and the effect made permanent by the passing of the material through drying ovens. In one of these modifications, a non-pressure sensitive adhesive composition is coated on the surface of an extruded film or filament and the absorbent applied on the surface of the solvent wetted film prior to passage through the ovens. In such method, any organic solvent coatable adhesive composition may be employed. In a second modification of this general method, a pressure-sensitive coating adhesive composition is coated on the face of an extruded film or filament, the solvent removed from the coated film or filament and the absorbent applied to the surface.

The absorbent product prepared by any one of the foregoing methods, particularly the products in the shape of films, may be further modified to form a discontinuous planar surface. Such surface may be reticulated or may contain embossed patterns of protrusions and depressions. Reticulated films are of special value for superior rate of fluid uptake. Preparation of absorbent products of films with discontinuous surfaces may be carried out in accordance with procedures well known in the art.

The following examples illustrate the invention but are not to be construed as limiting:

EXAMPLE I

An extrudable composition of 100 parts by weight of a styrene-isoprene-styrene (S-I-S) block copolymer (Kraton 1107) and 100 parts by weight of polyacrylate powder (Permasorb AG) are thoroughly blended at about 250° F. and the resulting molten blend cooled, pelletized and the pellets extruded at about 350° F. to form a film 3 mils in thickness with absorbent dispersed throughout. The film product swells immediately on contact with water.

EXAMPLE II

An extrudable composition of 100 parts by weight of styrene-butadiene-styrene (S-B-S) block copolymer (Kraton 1102) and 40 parts by weight polyacrylate powder (Sanwet) are blended, pelletized and extruded as described in Example I to form a film 10 mils in thickness with the absorbent dispersed throughout. The film products absorbs water rapidly.

EXAMPLE III

An absorbent composition suitable for film formation by solvent casting and of the following formulation:
  S-I-S rubber (Kraton 1107): 100 parts by weight
  Starch polyacrylate (SPG 5025): 100 parts by weight
  Zinc dibutyl dithiocarbamate: 5 parts by weight
  2,5-Ditertiary-butylhydroquinone: 1 part by weight
  Solids in toluene: 50 percent
is prepared by solvating the rubber and antioxidants in toluene and thereafter stirring in the starch polyacrylate absorbent. The composition is cast on a silicone liner at a dry coating weight of 2.0 ounces per square yard and the solvent thereafter evaporated to obtain absorbent film product having good absorptive properties.

EXAMPLE IV

A composition suitable for solvent casting of the following formulation:
  S-I rubber (Solprene 311): 100 parts by weight
  Polyacrylate (Permasorb-AG): 30 parts by weight
  Zinc dibutyl dithiocarbamate: 5 parts by weight
  2,5-ditertiary-butylhydroquinone: 1 part by weight
  Solids in toluene: 50 percent
is prepared by solvating the rubber and antioxidants in toluene and thereafter stirring in the polyacrylate absorbent. The composition is cast on a silicone liner at a dry coating weight of 3.0 ounces per square yard and the solvent then evaporated to obtain absorbent film product.

EXAMPLE V

In a manner similar to that described in Examples III and IV, an absorbent film product of 3.0 mils is obtained by casting the following film forming composition:
  S-B-S rubber (Kraton 1102): 100 parts by weight
  Cross-linked carboxymethylcellulose: 20 parts by weight
  Zinc dibutyl dithiocarbamate: 5 parts by weight
  2,5-ditertiary-butylhydroquinone: 1 part by weight
  Solids in toluene: 50 percent
The film rapidly absorbs free water on contact.

EXAMPLE VI

A 1 mil thermoplastic elastomeric film of S-I-S block copolymer (Kraton 1107) is solvent coated with the following pressure-sensitive adhesive formulation:
S-I-S rubber (Kraton 1107): 50 parts by weight
S-I rubber (Solprene 311): 50 parts by weight
Tackifier resin (Wing-tack 95): 80 parts by weight
Zinc dibutyl dithiocarbamate: 2 parts by weight
2,5-ditertiary-butylhydroquinone: 1 part by weight The adhesive composition is applied in amounts sufficient to deposit the pressure-sensitive adhesive on the film at the rate of 1 ounce per square yard and the resulting coated film passed through drying ovens maintained at 250° F. After the film is thoroughly dried, a cross-linked carboxymethylcellulose absorbent (Permasorb 10, National Starch) is uniformly applied to the surface of the film to produce a non-disintegrative absorbent product having the absorbent uniformly distributed on one surface thereof. The absorbent product on contact with an aqueous system shows immediate absorption of aqueous fluid. (Wing-tack 95 is predominantly polymerized piperylene-isoprene tackifier resin from Goodyear Tire & Rubber.)

EXAMPLE VII

A 1 mil thermoplastic-elastomeric film of S-I-S block copolymer (Kraton 1107) is coated with the following adhesive formulation at 1 ounce per square yard:
S-I-S rubber (Kraton 1107): 100 parts per weight
Resin (Amoco 18-290): 75 parts by weight
Zinc dibutyl dithiocarbamate: 2 parts by weight
2,5-ditertiary-butylhydroquinone: 1 part by weight
Solids in toluene: 50 percent by weight
(Amoco 18-290 is poly($\alpha$-methylstyrene) resin offered by Amoco Chemical Co.)

To the surface of the freshly coated film, particulate starch polyacrylate absorbent, (SGP 5025, General Mills or Henkel), is applied in a substantially monomolecular layer and the resulting film passed through drying ovens (maintained at about 250° F.) to remove the toluene solvent and to obtain an absorbent film product bearing absorbent on one major surface thereof. The resulting film shows immediate absorption when contacted with saline solution.

EXAMPLE VIII

Radial S-I-S block copolymer is extruded at 350° F. as a film and granular starch polyacrylate absorbent (Stasorb, A. E. Staley Company) is applied on the surface of the molten curtain. The curtain is allowed to cool to obtain a non-disintegrative absorbent product bearing absorbent on one major surface thereof. The product shows good absorptive properties.

EXAMPLE IX

The composition of Example I is prepared for extrusion and extruded to form a monofilament about 1 mil in diameter. The monofilament on contact with water absorbs water and forms a swollen rope.

The absorbent products of the present invention are useful in many articles where absorption of aqueous fluid is desired, such as diapers, bandages, pads, blankets and the like. The products are especially adapted to be employed in the manufacture of certain articles.

The absorbent product in the configuration of a film may be employed as the absorbent layer in a novel thin diaper of less bulk than a fabric diaper but of high absorptive capability. For such use, the absorbent film product may be either one having the absorbent dispersed throughout the film or one having the absorbent dispersed on one surface of the film. When the film product has absorbent dispersed throughout the film, it is desirable that the product be faced with a liquid permeable facing sheet 21 and be backed with a liquid impermeable backing sheet 22 and joined by conventional means to form a diaper 20 seen in FIG. 7. The facing sheet may be of a conventional fluid permeable cellulosic material. The backing sheet may be of conventional fluid impermeable material such as polyethylene but it is desirable that it be of a thermoplastic-elastomeric film such as used in the absorbent product and also of the same composition as the backing film described in U.S. Pat. No. 4,024,312. Such a diaper having a stretchable absorbent layer and elastic backing layer permits the diaper to be thin and of a surface area sufficient only to provide a snug fit around the wearer. The expansion of the absorbent product which occurs in use would be accompanied by a concurrent expansion of the backing layer, the expansion taking place only in amounts sufficient to accommodate the swollen absorbent product.

When the film product is one that has absorbent dispersed on one side of the film, the film product may serve the function of both the adsorbent layer and the backing layer, the side of the film not bearing the absorbent serving as a backing layer and automatically expanding on absorption. The absorbent film in the latter embodiment generally would be of a heavier gauge which can be determined readily be the skilled in the art.

A film product having absorbent dispersed throughout the matrix may also be employed as a coating on a substrate. In such application, an extrudable composition or a film forming solvent casting composition previously described is extruded or cast onto a substrate film in a conventional manner. In addition to coated films, coated filament may be produced wherein a filament or rope substrate bears the absorbent product as a coating as seen in FIG. 6.

The absorbent product having absorbent dispersed throughout the matrix may be extruded through a die fitted with a cylindrical orifice to produce a rope or flexible rod. By the use of a cross-head die, a supporting element in the form of a string, monofilament or wire may be coated with a composition such as the one previously described to obtain a coated core substrate which may serve as the basis of a slender tampon 25 such as illustrated in FIG. 8. Such tampon may be of a conventional length but have a diameter in the range of about 50 mils to about 400 mils. The advantage of a tampon made of the absorbent product of the present invention is the slender quality of the article to provide for ease in insertion while still having the same or greater absorptive capacity as a tampon of much larger dimensions.

EXAMPLE X

A composition consisting of a 30 percent solids dispersion in toluene of 100 parts by weight of Kraton 1107 and 100 parts by weight of starch acrylate absorbent (hydrolyzed starch acrylonitrile graft copolymer) is prepared by dispersing Kraton 1107 in toluene and thereafter rapidly stirring in starch acrylate absorbent. The composition is cast onto silicone paper and the solvent evaporated to obtain a flexible, elastic absorbent film of about 10 mils in thickness which absorbs more than ten times its weight of water becoming a gelatinous rubbery film.

The film is incorporated between a water-permeable diaper facing and water-impermeable diaper backing to produce an absorbent diaper having a thickness approximately 20 to 25 mils compared to a thickness of about 140 mils for a conventional diaper.

EXAMPLE XI

The extrudable composition of Example I is extruded intermittently via a cross-head die onto a cotton string forming intermittently coated lengths, each coated length being about $1.7 \times 10^3$ mils in length of about 200 mils in diameter. On completion of the extrusion, the string is cut in the uncoated part to form slender tampons.

I claim:

1. An elastic non-disintegrative absorbent product having a thickness ranging from about 1 to 60 mils comprising a water-insoluble substantially non-swelling matrix of an elastomeric polymer bearing uniformly dispersed and at least partially imbedded therein particulate water-insoluble water-swellable organic polymer absorbent wherein said elastomeric polymer comprises a thermoplastic elastomeric A-B-A or A-B block copolymer in which A represents an alkenylarene polymer block and in which B represents a polymer block of a conjugated lower aliphatic diene or lower aliphatic alkene and wherein said water-insoluble, water-swellable organic polymer absorbent is a cross-linked polymer having an average molecular weight per cross-linkage in the range of from about 13,000 to about 276,000.

2. A product according to claim 1 in which the absorbent has a particle size of from about 1 micron to about $2 \times 10^4$ microns in cross section and comprises from about 5 to about 200 parts per 100 parts by weight of matrix polymer.

3. A product according to claim 1 in which the product is in the form of a film.

4. A product according to claim 1 in which the product is in the form of a monofilament or rope.

5. A product according to claim 1 in which the elastomeric polymer is a thermoplastic-elastomeric A-B-A or A-B block copolymer or a mixture thereof in which the polymer absorbent is a synthetic acrylate polymer or an acrylate modified polysaccharide.

6. A thin absorbent article comprising an absorbent product of claim 5 faced with a liquid permeable sheet.

7. An article according to claim 6 in which the absorbent product is, in addition, backed with a liquid impermeable sheet.

8. A tampon comprising the absorbent product of claim 5.

* * * * *